(12) United States Patent
Miki et al.

(10) Patent No.: US 7,161,047 B2
(45) Date of Patent: Jan. 9, 2007

(54) PROCESS FOR PREPARING SECONDARY ALCOHOL

(75) Inventors: Yasushi Miki, Osaka (JP); Daisuke Fukumoto, Osaka (JP); Masafumi Mikami, Osaka (JP)

(73) Assignee: Daiso Co., Ltd., Osaka-Fu (JP)

( * ) Notice: Subject to any disclaimer, the term of this patent is extended or adjusted under 35 U.S.C. 154(b) by 0 days.

(21) Appl. No.: 11/091,487

(22) Filed: Mar. 29, 2005

(65) Prior Publication Data

US 2005/0222470 A1    Oct. 6, 2005

(30) Foreign Application Priority Data

Mar. 31, 2004 (JP) .............................. 2004-104782

(51) Int. Cl.
*C07C 29/56* (2006.01)
*C07C 29/153* (2006.01)
*C07C 29/157* (2006.01)
*C07C 29/158* (2006.01)

(52) U.S. Cl. ...................................... 568/907; 568/908

(58) Field of Classification Search ................ 568/907, 568/908
See application file for complete search history.

(56) References Cited

U.S. PATENT DOCUMENTS 3,956,405 A    5/1976   Katsushima et al.
6,166,269 A   12/2000   Chaudhari et al.

OTHER PUBLICATIONS

L. M. Schultze et al., "Practical Synthesis of the anti-HIV Drug, PMPA", Tetrahedron Letters, vol. 39, pp. 1853-1856, 1998.
P. S. Dragovich et al., "Palladium Catalyzed, Regioselective Reduction of 1,2-Epoxides by Ammonium Formate", J. Org. Chem., vol. 60, pp. 4922-4924, 1995.
H. Sajiki et al., "Pd/C(en)-Catalyzed Regioselective Hydrogenolysis of Terminal Epoxides to Secondary Alcohols", Chem. Commun., pp. 1041-1042, 1999.
M. Couturier et al., "The use of Borane-Amine Adducts as Versatile Palladium-Catalyzed Hydrogen-Transfer Reagents in Methanol", Tetrahedron Letters, vol. 42, pp. 2763-2766, 2001.
M. Ito et al., "Highly Efficient Chemoselective Hydrogenolysis of Epoxides Catalyzed by a $(\eta^5\text{-}C_5(CH_3)_5)$Ru Complex Bearing a 2-(Diphenylphosphino)ethylamine Ligand", Organometallics, vol. 22, No. 21, pp. 4190-4192, Oct. 13, 2003.

*Primary Examiner*—Elvis O. Price
(74) *Attorney, Agent, or Firm*—Wenderoth, Lind & Ponack, L.L.P.

(57) ABSTRACT

A process for preparing a secondary alcohol which is characterized in adding a primary or a secondary amine in the reaction system in case that the secondary alcohol is prepared by hydrogenating in the presence of a noble metal, an epoxy derivative represented by the following formula,

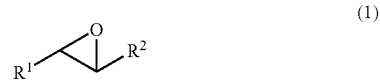

(1)

wherein $R^1$ and $R^2$ are the same or different, an organic group not containing aldehyde group or ketone group therein or hydrogen atom, provided that both $R^1$ and $R^2$ are not simultaneously hydrogen atom.

10 Claims, No Drawings

PROCESS FOR PREPARING SECONDARY ALCOHOL

TECHNICAL FIELD

The present invention relates to a novel process for preparing a secondary alcohol which is useful as an intermediate for synthesizing medicines such as antiarrhythmic drugs, physiologically active compounds or functional materials such as liquid crystal, etc.

BACKGROUND OF THE INVENTION

An optically active medicine or its intermediate is generally required to be highly chemical purity and highly optically purity. Therefore, it is a very important problem to establish the process for preparing an optically active secondary alcohol with highly chemical purity and highly optically purity.

As one of the methods for preparing an optically active secondary alcohol, it is known that an optically active secondary alcohol is prepared by hydrogenating an optically active 1,2-epoxide in the presence of palladium catalyst. According to this method, there is obtained not only an object secondary alcohol, but also its position isomer, a primary alcohol. In order to prevent the production of a primary alcohol, various studies have been done.

For example, the following methods (a) to (d) are reported.

(a) The reaction is carried out in the presence of sodium hydroxide in catalytic amount (Lisa M. SCHULTZE et al., Tetrahedron Lett., Vol. 39, p1853–1856 (1998)).

(b) The reaction is carried out in the coexistence of ammonium formate (Peter S. DRAGOVICH et al., J. Org. Chem., Vol.60, p4922–4924 (1995)).

(c) The reaction is carried out in the presence of palladium-ethylenediamine complex as catalyst (Hironao SAJIKI et al., Chem. Commun., p1041–1042 (1999)).

(d) The reaction is carried out in the coexistence of borane-tert-butylamine complex (Michel COUTURIER et al., Tetrahedron Lett., Vol.42, p2763–2766 (2001)).

In case of above method (a), it is possible to prevent the production of a primary alcohol, but the corresponding ketone is prepared in the course of the reaction. As many of the ketones are resemble to the object secondary alcohol in boiling point, and they are hardly separated and isolated by the usual separation method such as distillation, etc.

In case of above method (b), an excess amount of ammonium formate is required. In case of above methods (c) and (d), the respective amine complex must be previously prepared.

Therefore, there has been much room for improvement of the above known methods for preparing a secondary alcohol from the view point of the industrial production.

The present inventors have been earnestly studied to solve the above problems and as a result, have been found that when preparing a secondary alcohol by hydrogenating a 1,2-epoxy derivative in the presence of palladium catalyst, only by adding thereto a small amount of an amine, productions of not only a primary alcohol, but also the corresponding alkane and ketone as by-products, are prevented and that the object secondary alcohol is prepared in a mild condition with highly chemical purity and highly optical purity. Thus the present invention has been completed.

DETAILED DESCRIPTION OF THE PREFERRED EMBODIMENTS

The present invention relates to a process for preparing a secondary alcohol represented by the following formula,

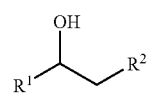

(2)

wherein $R^{1a}$ and $R^{2a}$ are the same or different, hydrogen atom, optionally unsaturated C1–10 alkyl group, halogeno C1–10 alkyl group, optionally unsaturated C3–10 cycloalkyl group, C6–14 aryl group, aralkyl group, hydroxy substituted C1–10 alkyl group, C1–10 alkyloxy substituted C1–10 alkyl group, furyl substituted C1–10 alkyl group, or aryloxy substituted C1–10 alkyl group, provided that $R^{1a}$ and $R^{2a}$ are not simultaneously hydrogen atom, or the following formula,

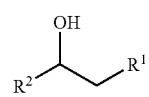

(3)

wherein $R^1$ and $R^2$ are the same as defined above, provided that $R^2$ is not hydrogen atom, which is characterized in adding a primary amine or a secondary amine in the reaction system in case that the secondary alcohol (2) or (3) is prepared by hydrogenating in the presence of a noble metal, an epoxide derivative represented by the following formula,

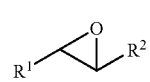

(1)

wherein $R^1$ and $R^2$ are the same as defined above, provided that both $R^1$ and $R^2$ are not simultaneously hydrogen atom.

The present invention relates to preferably, a process for preparing a secondary alcohol represented by the following formula,

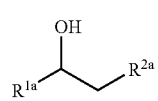

(2a)

wherein $R^{1a}$ and $R^{2a}$ are the same or different, hydrogen atom, optionally unsaturated C1–10 alkyl group, halogeno C1–10 alkyl group, optionally saturated C3–10 cycloalkyl group, C6–14 aryl group, aralkyl group, hydroxy substituted C1–10 alkyl group, C1–10 alkyloxy substituted C1–10 alkyl group, furyl substituted C1–10 alkyl group, or aryloxy substituted C1–10 alkyl group, provided that $R^{1a}$ and $R^{2a}$ are not simultaneously hydrogen atom, or the following formula,

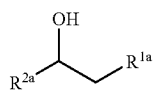

(3a)

wherein $R^{1a}$ and $R^{2a}$ are the same as defined above, provided that $R^{2a}$ is not hydrogen atom, which is characterized in adding a primary amine or a secondary amine in the reaction system in case that the secondary alcohol (2a) or (3a) is prepared by hydrogenating in the presence of a noble metal, an epoxy derivative represented by the following formula,

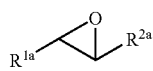

(1a)

wherein $R^{1a}$ and $R^{2a}$ are the same as defined above, provided that both $R^{1a}$ and $R^{2a}$ are not simultaneously hydrogen atom.

According to the present invention, when an epoxy derivative (1) or (1a) is used in the optically active form, the objective optically active secondary alcohol can be obtained in highly chemical purity without racemization.

The principle to prevent the production of a ketone compound as a by-product consists in converting a producing ketone compound into an amine compound chemically and physically different from the ketone compound by adding a primary or secondary amine. By doing so, the purification of the objective secondary alcohol becomes easy and it becomes possible to obtain the secondary alcohol in higher purity which is required in the field of medicinal manufacturing, etc.

Although reductive amination of a ketone compound in the presence of a noble metal such as palladium or platinum is known, the present invention wherein a secondary alcohol in higher purity is obtainable by coexisting this reaction together with hydrogenation reaction of an epoxy derivative, has not been reported and is a novel finding.

PREFERRED EMBODIMENTS FOR CARRYING OUT THE INVENTION

An epoxy derivative (1) or (1a) used in this reaction is usable of commercialized one or otherwise obtainable by cyclization of a halohydrin derivative, oxidation of an olefine compound and so on.

Substituents $R^1$ and $R^2$ in the formula (1) are not limited except a group which inhibits the present reaction such as aldehyde group or keto group therein, or a group which is effected by the present reaction and as far as the secondary alcohol is producible as a reaction product. Substituents $R^1$ and $R^2$ may be the same or different.

Preferable substituents $R^{1a}$ and $R^{2a}$ in the formula (1a) are optionally unsaturated C1–10 alkyl group such as hydrogen atom, methyl group, ethyl group, propyl group, isopropyl group, n-butyl group, sec-butyl group, tert-butyl group, n-pentyl group, isopentyl group, neopentyl group, n-hexyl group, n-decyl group, allyl group, 3-butenyl group, 5-hexenyl group, etc.; halogeno C1–10 alkyl group such as monochloromethyl group, etc.; optionally unsaturated C3–10 cycloalkyl group such as cyclohexyl group, 1-cyclohexenyl group, etc.; C6–14 aryl group such as phenyl group, naphthyl group, etc.; aralkyl group such as benzyl group, phenethyl group, cinnamyl group, etc.,; hydroxy substituted C1–10 alkyl group such as hydroxymethyl group, etc.; C1–10 alkyloxy substituted C1–10 alkyl group such as methoxymethyl group, etc.; furyl substituted C1–10 alkyl group such as furfuryl group etc.; aryloxy substituted C1–10 alkyl group such as phenoxymethyl group, etc. More preferably $R^{1a}$ is C1–10 straight or branched alkyl group, or C6–10 aryl group, and $R^{2a}$ is hydrogen atom. Especially preferable compounds of the formula (1a) are 1,2-epoxybutane, 1,2-epoxypentane, 1,2-epoxyhexane and 1,2-epoxyoctane.

The amines used in the present invention are not limited as long as the amines can reductively aminate the ketones produced as by-product, such as a primary amine, e.g., methylamine, ethylamine, allylamine, n-butylamine, isobutylamine, tert-butylamine, cyclohexylamine, aniline, benzylamine, ethylenediamine, etc., a secondary amine, e.g., dimethylamine, diethylamine, diisopropylamine, dicyclohexylamine, pyrrolidine, piperidine, morpholine, etc. The amount of the amine is theoretically equimolar with the ketone produced as by-product, and preferably 0.01 to 1 mole, more preferably 0.01 to 0.2 mole, most preferably 0.01 to 0.12 mole to an epoxy derivative (1) or (1a).

The noble catalyst used in the present invention includes catalyst supporting a noble metal such as palladium or platinum on a carrier such as carbon, alumina, silica, zeolite, an alkaline earth metal carbonate or a non-supported noble metal, an oxidized noble metal alone, or a mixture thereof. These may be a dried or wet form.

In the present invention, when the epoxy derivative (1) or (1a) is solid, the reaction is carried out in an organic solvent wherein it can dissolve, and when it is a liquid, the reaction can be carried out in an organic solvent or without any solvent. The organic solvent unlimitedly includes an alcohol-solvent such as methanol, ethanol, 2-propanol, etc., an ester-solvent such as ethyl acetate, butyl acetate, etc., an ether-solvent such as ethyl ether, tert-butylmethyl ether, etc., a halogeno compound-solvent such as chloroform, 1,2-dichloroethane, etc., a hydrocarbon-solvent such as toluene, n-hexane, etc. The amount of the organic solvent is suitably 0.5 to 40 (w/w) times as much as the amount of the epoxide derivative (1) or (1a).

The merits of the present invention consists in obtaining an objective secondary alcohol in high purity with a very simple method such as a conventional purification method, e.g., distillation, chromatography, etc., without using the rectification which requires high techniques. Furthermore, when using an optically active epoxy derivative, the corresponding optically active secondary alcohol can be obtainable without racemization.

The present invention is explained by the following examples, but the present invention should not be limited by these examples.

EXAMPLE 1

2-Octanol

To a 50-ml reaction vessel were added 1,2-epoxyoctane (2.56 g, 20.0 mmol), methanol (18 mL), 10% palladium/carbon containing 50% water (425 mg, Pd: 0.20 mmol) and catalytic amount of an amine subsequently, and then the mixture was vigorously stirred under an atmosphere of hydrogen at 25° C. Twenty to forty hours later, 10% palladium/carbon was removed by filtration and methanol was removed by distillation. The selectivity of thus obtained colorless oil was checked by gas chromatographic analysis. The results obtained by adding a various amines and other additives were respectively shown as follows:

TABLE 1

| | Additive | Production ratio (%) | | | |
|---|---|---|---|---|---|
| | (equiv.) | 2-Octanol | 1-Octanol | 2-Octanone | Octane |
| Example 1-1 | n-BuNH$_2$ (0.01) | 98 | 2 | 0 | 0 |
| Example 1-2 | Et$_2$NH (0.10) | 98 | 2 | 0 | 0 |
| Comparative example 1 | None | 67 | 8 | 2 | 23 |
| Comparative example 2 | NaOH (0.01) | 95 | 1 | 3 | 1 |
| Comparative example 3 | Na$_2$CO$_3$ (0.01) | 95 | 1 | 3 | 1 |
| Comparative example 4 | NaHCO$_3$ (0.10) | 94 | 1 | 4 | 1 |
| Comparative example 5 | AcONa (0.01) | 95 | 1 | 3 | 1 |
| Comparative example 6 | AcONH$_4$ (0.01) | 96 | 2 | 2 | 0 |
| Comparative example 7 | Et$_3$N (0.01) | 95 | 2 | 3 | 0 |

EXAMPLE 2

(S)-2-Hexanol

To a 1-liter reaction vessel were added (R)-1-chloro-2-hexanol (90.2 g, 660 mmol), methanol (110 mL) and an aqueous 24% NaOH solution (132 g, 792 mmol), and the mixture was stirred at 10° C. for 3 hours. Thereto was added an aqueous NaCl solution to separate with a separating funnel and the solvent was removed by distillation to give crude (R)-1,2-epoxyhexane. Thereto was added methanol (550 mL), 10% palladium/carbon containing 50% water (14.0 g) and n-butylamine (2.41 g, 33 mmol), and the mixture was vigorously stirred at 25° C. under an atmosphere of hydrogen. Twenty hours later, 10% palladium/carbon was removed by filtration, and the filtrate was distilled to give objective (S)-2-hexanol (47.2 g, yield: 70%, chemical purity: 99%, optical purity: 99% ee) as a colorless transparent oil.

Optical purity of the 2-hexanol is calculated on its area ratio by using gas chromatography after acetylation of the 2-hexanol.

Conditions

Column: CHIRALDEX G-TA by ASTEC Company (30 m×0.25 mm I.D.)

Column temperature: 45° C.

Sprit ratio: 100/1

Carrier gas: N$_2$ 1 ml/min.

Retention time: (S) compound, 10.0 min., (R) compound, 10.8 min.

EXAMPLE 3

(S)-2-Pentanol

To a 300-ml reaction vessel were added (R)-1,2-epoxypentane (38.8 g, 450 mmol), methanol (80 mL), 5% palladium/carbon containing 55% water (3.88 g) and n-butylamine (1.65 g, 22.5 mmol), and the mixture was vigorously stirred at 30° C. under atmosphere of hydrogen. Fifty hours later, 5% palladium/carbon was removed by filtration, and the filtrate was distilled to give objective (S)-2-pentanol (28.3 g, yield: 71%, chemical purity: 99%, optical purity: 99% ee) as a colorless transparent oil.

The measurement of optical purity is carried out in the same manner as Example 2.

Retention time: (S) compound: 9.1 min., (R) compound: 10.3 min.

EXAMPLE 4

(S)-2-Butanol

To a 300-mL reaction vessel (R)-1,2-epoxybutane (29.8 g, 414 mmol), 10% palladium/carbon containing 50% water (1.49 g) and n-butylamine (1.51 g, 20.7 mmol), and the mixture was vigorously stirred at 30° C. under an atmosphere of hydrogen. Thirty hours later, 10% palladium/carbon was removed by filtration and the filtrate was distilled to give objective (S)-2-butanol (18.4 g, yield: 60%, chemical purity: 99%, optical purity: 99% ee) as a colorless transparent oil. The measurement of optical purity is carried out in the same manner as Example 2.

Retention time: (S) compound: 5.6 min., (R) compound: 6.1 min.

The invention being thus described, it will be obvious that the same may be varied in many ways. Such variations are not to be regarded as a departure from the spirit and scope of the invention, and all such modification as would be obvious to one skilled in the art are intended to be included within the scope of the following claims.

What is claimed is:

1. A process for preparing a secondary alcohol represented by formula (2a),

(2a)

wherein R$^{1a}$ is optionally unsaturated C1–10 alkyl group, halogeno C1–10 alkyl group, optionally unsaturated C3–10 cycloalkyl group, aralkyl group, hydroxy substituted C1–10 alkyl group, C1–10 alkyloxy substituted C1–10 alkyl group, furyl substituted C1–10 alkyl group, or aryloxy substituted C1–10 alkyl group, and R$^{2a}$ is hydrogen atom, which comprises reacting a primary amine or a secondary amine, a noble metal catalyst and an epoxy derivative represented by formula (1a),

(1a)

wherein R$^{1a}$ and R$^{2a}$ are the same as defined above, to obtain the secondary alcohol represented by formula (2a).

2. The process for preparing a secondary alcohol according to claim 1 wherein R$^{1a}$ is C1–10 alkyl and R$^{2a}$ is hydrogen atom.

3. The process for preparing a secondary alcohol according to claim 1 wherein the epoxy derivative (1a) is an optically active compound.

4. The process for preparing a secondary alcohol according to claim 1 wherein the noble metal catalyst is palladium.

5. The process for preparing a secondary alcohol according to claim 2 wherein the noble metal catalyst is palladium.

6. The process for preparing a secondary alcohol according to claim 3 wherein the noble metal catalyst is palladium.

7. The process for preparing a secondary alcohol according to claim 4 wherein the epoxy derivative (1a) is 1,2-epoxybutane, 1,2-epoxypentane, 1,2-epoxyhexane or 1,2-epoxyoctane.

8. The process for preparing a secondary alcohol according to claim 5 wherein the epoxy derivative (1a) is 1,2-epoxybutane, 1,2-epoxypentane, 1,2-epoxyhexane or 1,2-epoxyoctane.

9. The process for preparing a secondary alcohol according to claim 6 wherein the epoxy derivative (1a) is 1,2-epoxybutane, 1,2-epoxypentane, 1,2-epoxyhexane or 1,2-epoxyoctane.

10. The process for preparing a secondary alcohol according to claim 1 wherein the secondary alcohol (2a) is an optically active compound.

* * * * *